US010709365B2

(12) United States Patent
Cohen et al.

(10) Patent No.: US 10,709,365 B2
(45) Date of Patent: Jul. 14, 2020

(54) SYSTEM AND METHOD FOR NONINVASIVE ANALYSIS OF SUBCUTANEOUS TISSUE

(71) Applicant: I.r Med Ltd., Rosh-Pina (IL)

(72) Inventors: Yaniv Cohen, Jerusalem (IL); Ronnie Klein, Haifa (IL); Arkadi Zilberman, Beer Sheva (IL); Ben Zion Dekel, Hadera (IL); Nathan Blaunstein, Beer Sheva (IL)

(73) Assignee: I. R. Med Ltd., Rosh Pina (IL)

( * ) Notice: Subject to any disclaimer, the term of this patent is extended or adjusted under 35 U.S.C. 154(b) by 187 days.

(21) Appl. No.: 15/627,470

(22) Filed: Jun. 20, 2017

(65) Prior Publication Data

US 2017/0303829 A1 Oct. 26, 2017

Related U.S. Application Data

(63) Continuation-in-part of application No. 14/465,311, filed on Aug. 21, 2014, now abandoned.

(51) Int. Cl.
*A61B 5/1455* (2006.01)
*A61B 5/00* (2006.01)

(52) U.S. Cl.
CPC .......... *A61B 5/1455* (2013.01); *A61B 5/0059* (2013.01); *A61B 5/0075* (2013.01);
(Continued)

(58) Field of Classification Search
CPC ... A61B 5/0059; A61B 5/0075; A61B 5/1455; A61B 5/14551; A61B 5/14552; A61B 5/6815; A61B 5/6826; A61B 5/7235
See application file for complete search history.

(56) References Cited

U.S. PATENT DOCUMENTS

| 4,805,623 A * | 2/1989 | Jobsis ................ A61B 5/14551 |
| | | 250/339.12 |
| 5,086,229 A | 2/1992 | Rosenthal et al. |

(Continued)

FOREIGN PATENT DOCUMENTS

| WO | WO 2008/039299 | 4/2008 |
| WO | WO 2013/160780 | 10/2013 |

(Continued)

OTHER PUBLICATIONS

Notice of Allowance of U.S. Appl. No. 15/644,855, dated Feb. 19, 2020.

(Continued)

*Primary Examiner* — Eric F Winakur
*Assistant Examiner* — Chu Chuan Liu
(74) *Attorney, Agent, or Firm* — Pearl Cohen Zedek Latzer Baratz LLP

(57) ABSTRACT

A method for noninvasive analysis of subcutaneous tissue includes irradiating a surface of the tissue with short wave infrared (SWIR) radiation in a first spectral band that is strongly absorbed by water, and with SWIR radiation in a second spectral band such that an interaction of the radiation in both spectral bands with a component of the tissue other than water is substantially identical. An intensity of the radiation in each of the spectral bands that emerges from the tissue is measured. A relative absorption by the tissue of radiation in one of spectral bands relative to absorption by the tissue of radiation in the other of the spectral bands is calculated. A state of the tissue is determined in accordance with the calculated relative absorption.

19 Claims, 6 Drawing Sheets

(52) U.S. Cl.
CPC .......... *A61B 5/6815* (2013.01); *A61B 5/6826* (2013.01); *A61B 5/7235* (2013.01)

(56) References Cited

U.S. PATENT DOCUMENTS

| | | | |
|---|---|---|---|
| 5,188,108 | A | 2/1993 | Secke |
| 5,348,003 | A | 9/1994 | Caro |
| 5,355,880 | A * | 10/1994 | Thomas .............. A61B 5/02007 |
| | | | 128/925 |
| 5,524,617 | A | 6/1996 | Mannheimer |
| 5,974,337 | A | 10/1999 | Kaffka et al. |
| 6,289,230 | B1 | 9/2001 | Chaiken et al. |
| 6,662,031 | B1 | 12/2003 | Khalil et al. |
| 8,073,518 | B2 | 12/2011 | Chin |
| 8,100,834 | B2 | 1/2012 | Shuler |
| 8,750,952 | B2 * | 6/2014 | Aalders ................ A61B 5/0059 |
| | | | 600/310 |
| 2003/0139681 | A1 | 7/2003 | Melker |
| 2004/0230107 | A1 * | 11/2004 | Asada .................. A61B 5/0084 |
| | | | 600/335 |
| 2006/0122475 | A1 | 6/2006 | Balberg et al. |
| 2006/0200012 | A1 | 9/2006 | Mansour et al. |
| 2007/0112273 | A1 | 5/2007 | Rogers |
| 2008/0146906 | A1 * | 6/2008 | Baker .................. A61B 5/0059 |
| | | | 600/407 |
| 2008/0183388 | A1 | 7/2008 | Goodrich |
| 2010/0056928 | A1 | 3/2010 | Zuzak et al. |
| 2011/0118575 | A1 * | 5/2011 | Lloyd .................. A61B 5/0059 |
| | | | 600/328 |
| 2012/0010477 | A1 | 1/2012 | Amano et al. |
| 2013/0030267 | A1 | 1/2013 | Lisogurski et al. |
| 2013/0144136 | A1 | 5/2013 | Rymut |
| 2014/0200423 | A1 | 7/2014 | Eisen et al. |
| 2015/0051498 | A1 * | 2/2015 | Darty ..................... A61B 5/447 |
| | | | 600/477 |
| 2015/0157246 | A1 | 6/2015 | Leszinske |
| 2016/0051147 | A1 | 2/2016 | Cohen et al. |

FOREIGN PATENT DOCUMENTS

| | | |
|---|---|---|
| WO | WO 2014/105520 | 7/2014 |
| WO | WO 2015/167251 | 11/2015 |
| WO | WO 2016/069788 | 5/2016 |

OTHER PUBLICATIONS

PCT International Search Report and Written Opinion from corresponding PCT International Application No. PCT/IL2015/050839, dated Dec. 17, 2015.
U.S. Office Action from corresponding U.S. Appl. No. 14/465,311, dated Jul. 25, 2016.
U.S. Final Office Action from corresponding U.S. Appl. No. 14/465,311, dated Feb. 15, 2017.
EP Extended European Search from corresponding EP Appl No. 15834459.8., dated Apr. 11, 2018.
PCT International Search Report and Written Opinion from corresponding PCT International Application No. PCT/IL2018/050748, dated Dec. 13, 2018.
U.S. Office Action from corresponding U.S. Appl. No. 15/644,855, dated Jun. 12, 2019.
PCT International Search Report and Written from corresponding PCT International Application No. PCT/IL2016/051386, dated Apr. 4, 2017.

* cited by examiner

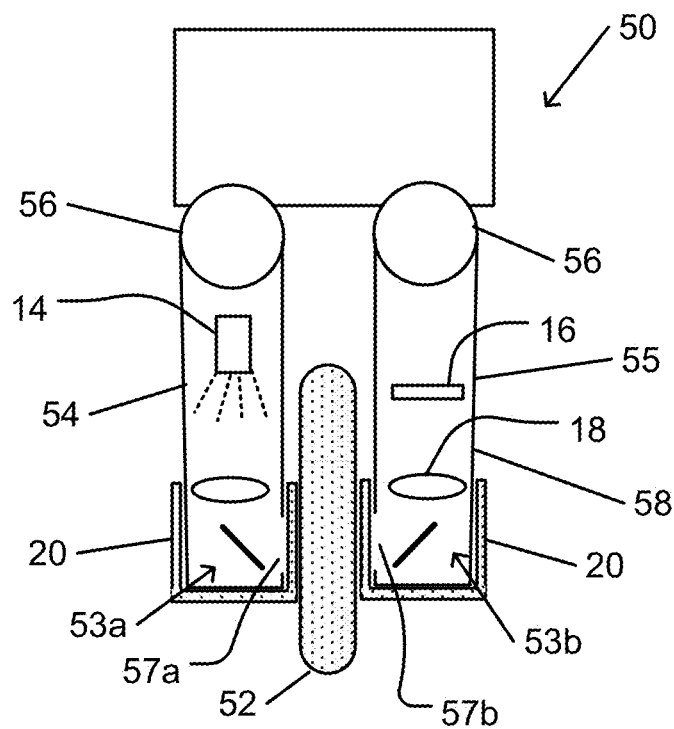
Fig. 2A
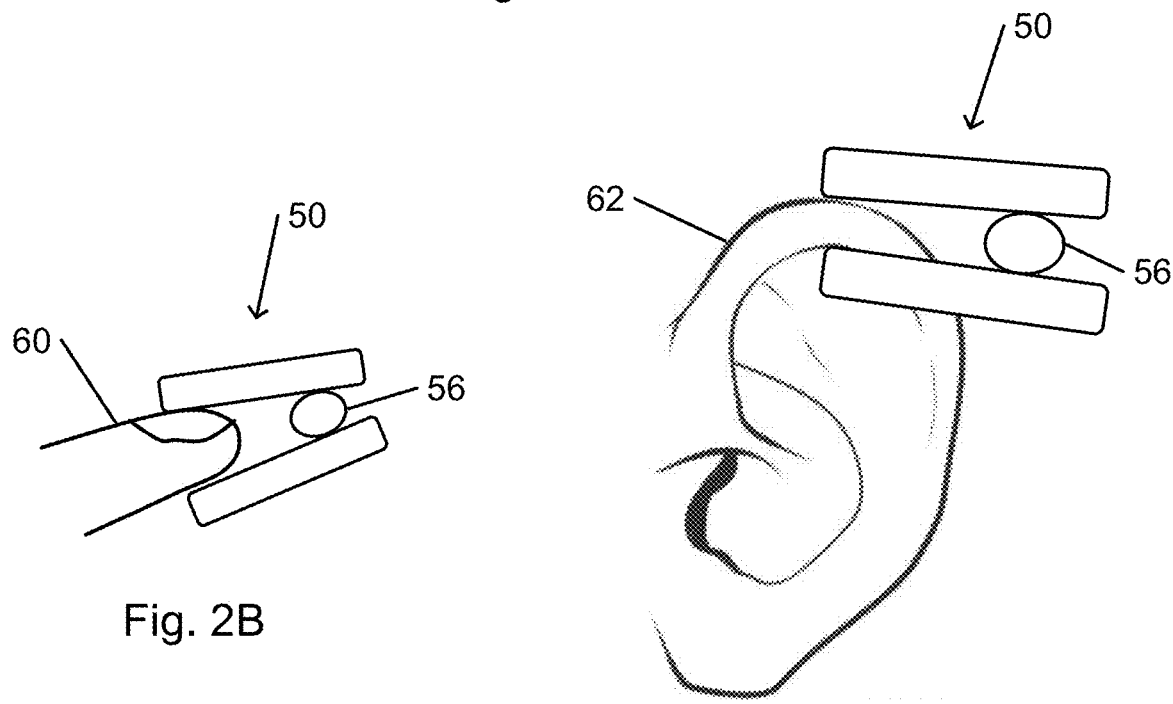
Fig. 2B
Fig. 2C

SYSTEM AND METHOD FOR NONINVASIVE ANALYSIS OF SUBCUTANEOUS TISSUE

CROSS REFERENCE TO RELATED APPLICATION

This application is a continuation-in-part of application Ser. No. 14/465,311, filed Aug. 21, 2014, which is incorporated herein by reference.

FIELD OF THE INVENTION

The present invention relates to noninvasive analysis. More particularly, the present invention relates to a system and method for noninvasive analysis of subcutaneous tissue.

BACKGROUND OF THE INVENTION

Various medical conditions are characterized by accumulation of liquids under or behind the skin surface. Such conditions may include otitis media, pressure ulcers, or other types of deep tissue injury under intact skin.

Medications or other substances may be introduced or delivered into the bloodstream. For example, a substance may be delivered orally to a patient, or may be injected into tissue or via an intravenous infusion. In some cases, it is important to monitor the concentration or amount of the substance in a patient's blood or tissue. Monitoring the concentration or the amount may include drawing a blood or tissue sample from the patient.

SUMMARY OF THE INVENTION

There is thus provided, in accordance with some embodiments of the present invention, a method for noninvasive analysis of tissue, the method including: irradiating a surface of the tissue with short wave infrared (SWIR) radiation in a first spectral band that is strongly absorbed by water, and with SWIR radiation in a second spectral band such that an interaction of the radiation in both spectral bands with a component of the tissue other than water is substantially identical; measuring an intensity of the radiation that emerges from the tissue in each of the spectral bands; calculating a relative absorption by the tissue of radiation in one of spectral bands relative to absorption by the tissue of radiation in the other of the spectral bands; and determining a state of the tissue in accordance with the calculated relative absorption.

Furthermore, in accordance with some embodiments of the present invention, the first spectral band is in the wavelength range of 1400 nm to 1500 nm.

Furthermore, in accordance with some embodiments of the present invention, the second spectral band is in the wavelength range of 1000 nm to 1350 nm or 1500 nm to 2100 nm.

Furthermore, in accordance with some embodiments of the present invention, a gap in wavelength between the first and second spectral bands is less than 200 nm.

Furthermore, in accordance with some embodiments of the present invention, measuring the intensity includes measuring the intensity of the radiation that is transmitted across the tissue (e.g., passing through the tissue and not reflected back towards the radiation source).

Furthermore, in accordance with some embodiments of the present invention, the tissue includes tissue of a finger or an ear.

Furthermore, in accordance with some embodiments of the present invention, measuring the intensity includes measuring the intensity of the radiation that is reflected by the tissue.

Furthermore, in accordance with some embodiments of the present invention, measuring the intensity includes measuring the intensity of the radiation that emerges from the tissue at a plurality of lateral distances from a location of the irradiating of the tissue.

Furthermore, in accordance with some embodiments of the present invention, the state of the tissue includes a concentration of a substance in blood.

Furthermore, in accordance with some embodiments of the present invention, the substance is an introduced substance.

There is further provided, in accordance with some embodiments of the present invention, a system for noninvasive analysis of tissue, the system including: at least one source of infrared radiation to irradiate the tissue, the infrared radiation including SWIR radiation in a first spectral band that is strongly absorbed by water, and including radiation in a second spectral band such that an interaction of the radiation in both spectral bands with a component of the tissue other than water is substantially identical; at least one radiation detector to measure an intensity of radiation in each of the two spectral bands that emerges from the tissue (e.g., reflected from the tissue or passing through the tissue, to come out at another side); and a processor that is configured to calculate a relative absorption by the tissue of radiation in one of spectral bands relative to absorption by the tissue of radiation in the other of the spectral bands and determine a state of the tissue in accordance with the calculated relative absorption.

Furthermore, in accordance with some embodiments of the present invention, wherein the at least one radiation detector is configured to measure the intensity of the radiation that emerges from a surface of the tissue that is irradiated by the at least one radiation source.

Furthermore, in accordance with some embodiments of the present invention, the at least one radiation detector is configured to measure the intensity of the radiation that emerges from the surface of the tissue at a plurality of lateral distances from the at least one radiation source.

Furthermore, in accordance with some embodiments of the present invention, the at least one radiation detector comprises a plurality of radiation detectors separated by different lateral distances from the at least one radiation source.

Furthermore, in accordance with some embodiments of the present invention, the at least one radiation detector is configured to measure the radiation that emerges from a surface of the tissue that is substantially opposite a surface of the tissue that is irradiated by the at least one radiation source.

Furthermore, in accordance with some embodiments of the present invention, the system includes a removable cover for placement over an aperture of the at least one radiation source or of the at least one radiation detector.

Furthermore, in accordance with some embodiments of the present invention, the at least one radiation source includes two radiation sources, one of the sources being configured to emit radiation in the first spectral band and the other being configured to emit radiation in the second spectral band.

Furthermore, in accordance with some embodiments of the present invention, the at least one radiation detector includes two radiation detectors, one of the detectors being configured to measure an intensity of radiation in the first spectral band and the other being configured to measure an intensity of radiation in the second spectral band.

Furthermore, in accordance with some embodiments of the present invention, the system includes a dispersive element to separate spectral components of the infrared radiation and a micro-mirror array, the micro-mirror array being operable to direct a selected spectral component of the infrared radiation to the tissue or to the at least one radiation detector.

Furthermore, in accordance with some embodiments of the present invention, the first spectral band is in the wavelength range of 1400 nm to 1500 nm.

Furthermore, in accordance with some embodiments of the present invention, the second spectral band is in the wavelength range of 1000 nm to 1350 nm or 1500 nm to 2100 nm.

There is further provided, in accordance with some embodiments of the present invention, a method for determining a state of tissue, the method including: irradiating a surface of the tissue with SWIR radiation in a first spectral band in the wavelength range 1300 nm to 1430 nm, and with SWIR radiation in a second spectral band such that an interaction of the radiation in both spectral bands with a component of the tissue other than water is substantially identical; measuring an intensity of the radiation that emerges from the tissue in each of the spectral bands; and calculating an absorption by the tissue of radiation in the two spectral bands, the absorption being indicative of the state of the tissue.

BRIEF DESCRIPTION OF THE DRAWINGS

In order for the present invention to be better understood and for its practical applications to be appreciated, the following Figures are provided and referenced hereafter. It should be noted that the Figures are given as examples only and in no way limit the scope of the invention. Like components are denoted by like reference numerals.

FIG. 2A is a schematic drawing of a measurement unit of a system for noninvasive analysis of subcutaneous liquids based on transmission of infrared radiation, in accordance with an embodiment of the present invention.

FIG. 2B schematically illustrates attachment of the measurement unit of FIG. 2A to a finger.

FIG. 2C schematically illustrates attachment of the measurement unit of FIG. 2A to an ear.

DETAILED DESCRIPTION OF THE INVENTION

Figure 1A:
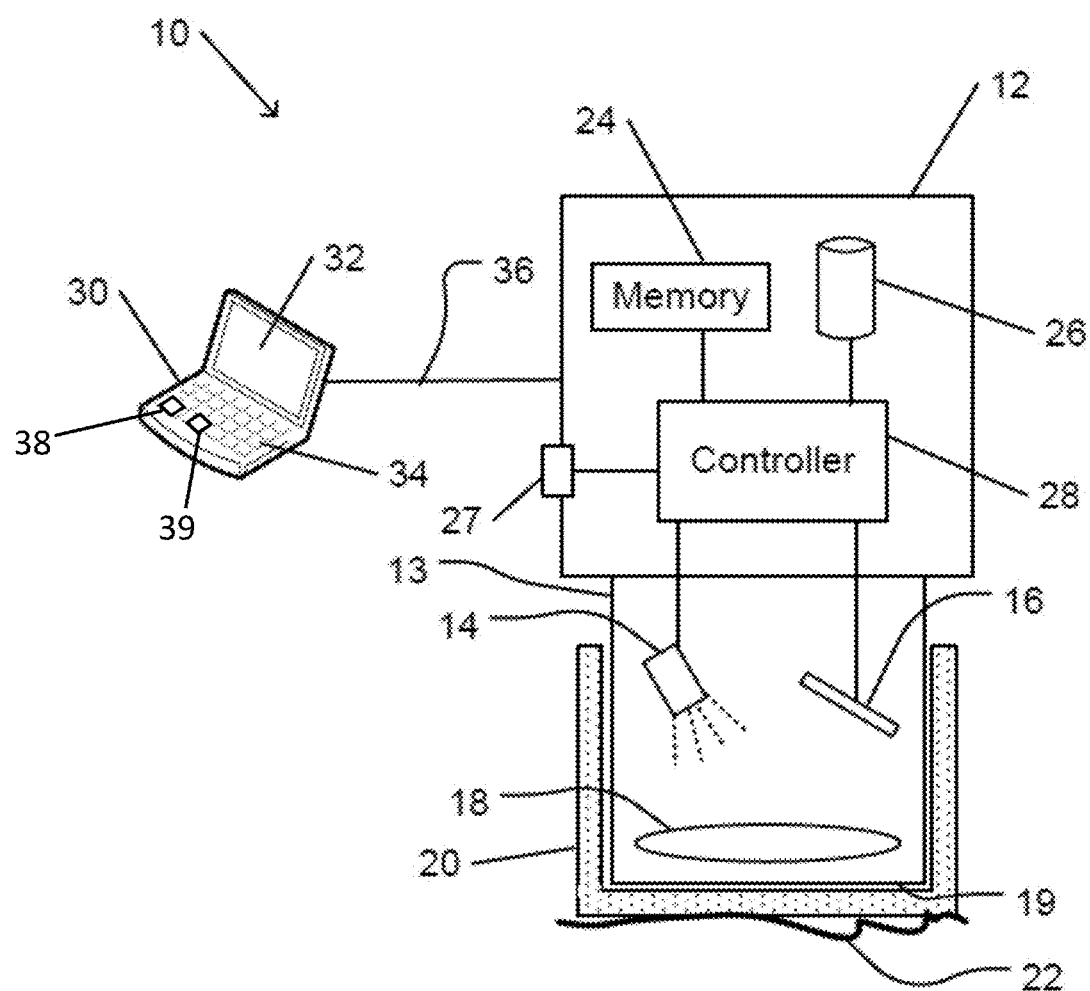
FIG. 1A is a schematic drawing of a system for noninvasive analysis of subcutaneous liquids based on reflection of infrared radiation, in accordance with an embodiment of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, us of the conjunction "or" as used herein is to be understood as inclusive (any or all of the stated options).

Some embodiments of the invention may include an article such as a computer or processor readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein.

In accordance with an embodiment of the present invention, reflection of radiation or transmission of radiation by tissue in a region of the body is measured. In some embodiments, reflected radiation may refer to radiation that emerges from the tissue via a surface through which the tissue was irradiated or illuminated. Thus, reflected radiation may result from one or more of radiation that is reflected from an interface between dissimilar media and radiation that is scattered in the backward direction. For example, a measurement unit may be placed on or near a surface of the tissue, e.g., a skin surface of the patient's body, an eardrum, or another surface. The measurement unit may include one or more radiation sources and one or more radiation detectors. The measurement unit may be configured to measure reflection. For example, the radiation sources may be configured to irradiate or illuminate a tissue surface (e.g., a skin surface of a patient). When irradiating the tissue surface, the radiation penetrates into the tissue. The radiation detectors may be aimed at the irradiated surface so as to detect radiation that is reflected or backscattered by the tissue that is covered by the surface. In other cases, the radiation sources and detectors may be configured to measure transmission of the radiation through the tissue. For example, measurement unit may be configured such that radiation that is emitted by the radiation sources is directed toward the radiation detectors. Thus, when tissue (e.g., a part of the patient's body such as an ear, finger, toe, fold of skin, or other part of the body) is placed in the optical path from the radiation source to the corresponding radiation detector, transmission of the radiation through the tissue may be measured.

The reflection or transmission measurement may be indicative of a state of the tissue. The tissue may include subcutaneous liquids such as blood or other fluids. In some embodiments, the term "subcutaneous", may refer to a depth within tissue, which may or may not be covered with skin. For example, subcutaneous liquid may be within or behind a membrane, such as within or behind the eardrum, or within lung tissue. The state of the tissue may be indicative of a medical condition in the patient. For example, a medical condition may include otitis media, early stages of pressure ulcers, or other types of deep tissue injury under intact skin in which liquids accumulate subcutaneously. A state of the tissue may include a concentration of a substance in the blood or other subcutaneous fluids. The substance (e.g., a medication, contrast agent, food component or supplement, or other administered product) may have been administered to the patient (e.g., orally, or via injection or infusion), may be a product of physiological processes on an administered substance, or may be produced by the patient's body. For example, the most common pressure ulcers are above the heel bone under the skin. The heel bone is covered with a thin fatty layer which is normally composed of triglycerides. When ischemia starts the triglycerides fatty tissue decomposes into glycerol and free fatty acids. According to some embodiments, a lookup table containing different concentrations of, for example, glycerol and free fatty acids may be created, and may further include data regarding such substances absorption (e.g., in different waivelenghes). A processor, may determine state of the tissue above the heel bone (or at any other location) by comparing the optical readings from the examined tissue, to the absorption values in the lookup table, and based on the determined concentration of the different substances, determine the existence and degree or severity of DTI.

The reflection or transmission is measured in at least two spectral bands of the shortwave infrared (SWIR) spectral region of the electromagnetic spectrum. As used herein, the SWIR spectral region is used to include the wavelength range of about 1000 nm to about 2500 nm. The shorter wavelengths of this spectral region are sometimes referred to as near infrared (NIR).

A first spectral band may be in a portion of the SWIR spectral region where radiation is strongly absorbed by water (e.g., in the wavelength band from about 1400 nm to about 1500 nm) as compared to adjacent or other bands. As used herein, radiation is considered to by strongly absorbed when absorption (e.g., as characterized by an absorption coefficient) is at least an order of magnitude (approximately 10 times or more) greater than in the comparison band.

A second spectral band is in an adjacent SWIR spectral band, e.g., in the wavelength band from about 1000 nm to about 1350 nm, or in the wavelength band from about (e.g., ±10%) 1500 nm to about 2100 nm. The second spectral band is sufficiently close to the first spectral band such that an interaction of radiation in both spectral bands (e.g., absorption or scattering) with tissue components other than water is substantially identical (e.g., having the same or very similar behaviorinteraction with the tissue). For example, absorption of radiation in the spectral band of about 1000 nm to about 1800 nm by such tissue components other than water such as hemoglobin, melanin, and other chromophores is approximately constant (with absorption coefficients in the range of about 0.1 $cm^{-1}$ to about 1 $cm^{-1}$). The scattering coefficient is about 5 $cm^{-1}$ to about 15 $cm^{-1}$. Thus, radiation may penetrate as deep as 8 cm to 10 cm into tissue.

For example, a gap between the two bands may be no more than 200 nm. In some cases, the gap between the two bands may be no more than 100 nm.

For example, two or more of the radiation sources may be configured to emit radiation in different spectral bands of the SWIR spectral region. As another example, two or more of the radiation detectors may be configured to detect different radiation in different spectral bands of the SWIR spectral region and/or the visible spectral region (also referred to as VIS). Both the radiation sources and the radiation detectors may be limited to particular spectral bands.

For example, the source or detector may include a wavelength selection arrangement that incorporates a spectrally dispersive element (e.g., a grating, prism, or spectrally selective optical coating), focusing optics (e.g., lenses or mirrors), and a micro-mirror array that contains individually rotatable micro-mirrors (or rotatable in groups). Radiation originating from the radiation source (for irradiating the tissue) or from the tissue (e.g., after reflection or transmission) may be focused onto the dispersive element to spatially separate different spectral components (e.g., wavelength ranges or spectral bands) of the radiation. For example, different wavelengths of the radiation may be directed in different directions. Spectrally separated radiation from the dispersive element may be focused onto the micro-mirror array. For example, each spectral component may be incident on a different micro-mirror of the array. Therefore, each micro-mirror may be selectively rotated to direct a particular spectral component of the radiation either toward or away from a source aperture (to irradiate the tissue surface) or a detector (to be detected as transmitted or reflected radiation).

In some cases, either the spectral bands in which radiation is emitted by different radiation sources, or the spectral bands to which different radiation detectors are sensitive, may partially or completely overlap. In such a case, spectral separation may be effected by another of the components (e.g., source, detector, or optics).

In biological tissue, the absorption of radiation in a particular spectral band (e.g., in the SWIR range) may be determined the contributions of various substances or chromophores that absorb electromagnetic radiation of different wavelengths. Chromophores are functional groups of molecules that absorb light or electromagnetic radiation to various extents in a spectral band. Each chromophore is characterized by a particular characteristic absorption as a function of wavelength, and which may be used to identify the presence of that molecule.

In practice, only a few chromophores contribute to the absorption in the NIR-SWIR range from about 800 nm to about 2400 nm. In this region, major contributions to absorption in the body arise from the presence of (oxy- or deoxy-) hemoglobin, water, and fat and melanin. Other chromophores that may potentially contribute slightly (e.g., about 1%-3%) to the absorption include myoglobin, cytochrome, bilirubin, lipids and other substances.

In SWIR radiation with wavelength greater than about 1000 nm, the contribution of water to absorption is greater than that of hemoglobin, melanin and other chromophores.

For example, one of the spectral bands may include the SWIR band from about 1400 nm to about 1500 nm, which is strongly absorbed by water. Another of the spectral bands may include the SWIR band from about 1000 nm to about 1350 nm, or the SWIR band from about 1500 nm to about 2100 nm. (Radiation in the spectral region from about 1350 nm to 1400 nm, where the absorption by water rapidly changes with wavelength (with a large slope in a curve of absorption versus wavelength), may not be used in some cases In some cases, a rate of change of absorption of radiation as a function of the wavelength may be measured in the spectral region from about 1300 nm to about 1430 nm. In this spectral region, the absorption by water rapidly changes with wavelength. The high rate of change of absorption with wavelength (absolute rate of change for absorption in 1 mm of water being greater than 0.007 $nm^{-1}$) may be exploited to detect the presence of water (or an amount or concentration of water) in the tissue. For example, a slope of a graph of absorption (or reflection or transmission) versus wavelength may be calculated. As an example, it may be noted that in FIG. 3, the slopes of normal tissue curve 72 and of disease tissue curve 74 (having different water content) noticeably differ from one another in the spectral range of 1300 nm to 1430 nm.

The measurement of the reflection or transmission may be performed in at least two different but adjacent spectral bands of the SWIR region of the electromagnetic spectrum. The results of the reflection or transmission measurement may be analyzed by comparison with previously measured or calibrated results. The comparison may be utilized to determine the state of the subcutaneous tissue.

For example, one of the spectral bands may be selected such that the reflection or transmission in that band is relatively unaffected by the presence or absence of the medical condition. The measured reflection or transmission in this spectral band may serve as a reference. For example, the reference measurement may set a baseline value or temporary calibration for measurements in the presence of conditions that are specific to the measurement. The conditions may be related to the patient's body (e.g., dimensions or other properties of a skin or tissue surface or body part on which the measurements are made). The conditions may be related to drift or transient variation in properties of the measurement unit that is used to perform the reflection or transmission measurements.

Measurements may be further calibrated by monitoring a dark signal (e.g., when a radiation detector is shielded from radiation) and an intensity of the radiation source (e.g., by providing a direct channel of radiation from the radiation source to the corresponding radiation detector).

Another of the spectral bands may be selected such that a reflection or transmission measurement in that band is sensitive to the state of the tissue. Thus, when adjusted in accordance with the various reference and calibration measurements, the measurement in that other spectral brand may be indicative of the state of the tissue. Thus, the state of the tissue may be detected noninvasively.

For example, one of the spectral bands may include wavelengths of SWIR electromagnetic radiation that are strongly (e.g., almost completely) absorbed by water. Another of the spectral bands may include SWIR electromagnetic radiation that is largely transmitted by water. In some cases, one of the spectral bands may include SWIR electromagnetic radiation whose absorption varies rapidly with wavelength (e.g., instead of, or in addition to, the spectral band in which radiation is strongly absorbed).

FIG. 1A is a schematic drawing of a system for noninvasive analysis of subcutaneous liquids based on reflection of infrared radiation, in accordance with an embodiment of the present invention.

Liquid analysis system 10 includes reflection measurement unit 12. Reflection measurement unit 12 includes infrared radiation source 14 and radiation detector 16. Unit aperture 19 on optical head 13 of reflection measurement unit 12 is configured to be placed on or near a tissue surface 22 of a patient so as to measure infrared radiation that is reflected from tissue that is covered by tissue surface 22. Liquid analysis system 10 is configured to determine the state of subcutaneous tissue, such as the presence of absence of a subcutaneous medical condition in tissue that is covered by tissue surface 22, or to measure the presence or absence of an administered substance in blood that flows via the tissue.

Reflection measurement unit 12 may be configured to be held and manipulated by a single hand of a user. For example, the user may include a healthcare professional, a caregiver, or the patient. Reflection measurement unit 12 may include an internal power source in the form of a battery or other self-contained power source, or may be connectable to an external power source. Reflection measurement unit 12, optical head 13, or both may have a generally or substantially cylindrical form, or may have another geometrical form or shape. Unit aperture 19 may thus have a substantially round or elliptic shape, or another shape.

Unit aperture 19 of optical head 13 may include one or more component apertures.

Figure 1B:
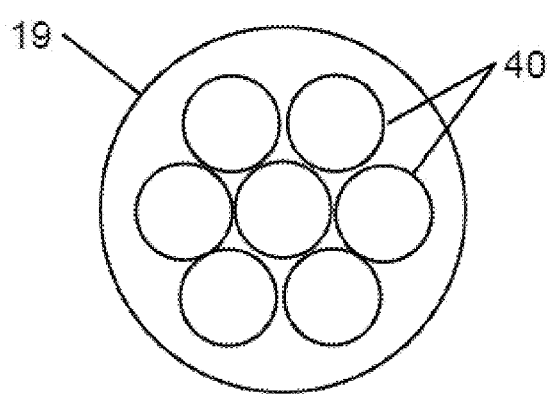
FIG. 1B is a schematic illustration of a plurality of component apertures of an optical head of the system shown in FIG. 1A.

FIG. 1B is a schematic illustration of a plurality of component apertures of an optical head of the system shown in FIG. 1A. Unit aperture 19 includes a plurality of component apertures 40. Each component apertures 40 may be configured to enable passage of radiation from a single component infrared source of infrared radiation source 14 or to a component detector of radiation (e.g., infrared) detector 16. In the configuration shown, unit aperture 19 is round and component apertures 40 are arranged in a hexagonal pattern. Other configurations may include other shapes of unit aperture 19 or other arrangements of component apertures 40.

Infrared radiation source 14 is configured to irradiate tissue surface 22 with SWIR radiation via unit aperture 19 of optical head 13. Infrared radiation source 14 may include one or more separate component infrared sources. For example, two or more component infrared sources may each produce SWIR radiation in one or more spectral bands. For example, infrared radiation source 14 may include tungsten-halogen or other incandescent lamp, a xenon lamp or other gas emission radiation source, a fluorescent radiation source, an electronic radiation source (e.g., light emitting diode, laser diode, or laser), or other radiation source.

Infrared radiation source 14 may include a single wideband infrared source that emits radiation over two or more spectral bands. In some cases, infrared radiation from a single wideband infrared source may be separately channeled via separate spectral band selection devices (e.g., that include filters, prisms, or gratings) to form effective single-band sources. For example, the separate channeling may be performed sequentially to radiate infrared radiation in different spectral bands in quick succession (e.g., less than a millisecond) via a single component aperture 40 of unit aperture 19. As another example, the radiation from the wideband source may be divided (e.g., using a beam splitter)

and concurrently channeled via different band-selection devices to concurrently radiate in different spectral bands via separate component apertures 40 of unit aperture 19.

Optics 18 of optical head 13 may direct infrared radiation from infrared radiation source 14 out unit aperture 19 (or from a component infrared source of infrared radiation source 14 out a component aperture 40 of unit aperture 19) to tissue surface 22. For example, optics 18 may include one or more mirrors, reflectors, light pipes or optical fibers, lenses, filters, gratings, polarizers, beam splitters, prisms, apertures, collimators, shutters, or other components. Similarly, optics 18 may direct radiation from tissue surface 22 (e.g., reflected radiation) via unit aperture 19 to infrared radiation detector 16 (or via a component aperture 40 of unit aperture 19 to a component detector of infrared radiation detector 16). One or more components of optics 18 may function both to direct radiation from infrared radiation source 14 to tissue surface 22, and to direct radiation from tissue surface 22 to infrared radiation detector 16. Alternatively or in addition, separate components of optics 18 may be provided for either directing radiation from infrared radiation source 14 to tissue surface 22 or for directing radiation from tissue surface 22 to infrared detector 16.

Optics 18 may be or may include a dispersive element (e.g., grating, prism, element with spectrally selective optical layers or coating, or another dispersive element), and a micro-mirror array for directing radiation of one or more selected wavelengths toward unit aperture 19 (e.g., for limiting irradiation of tissue surface 22 to selected wavelengths), or toward infrared detector 16 (e.g., for limiting detection of reflected or transmitted radiation to selected wavelengths).

Optics 18 may be configured to direct a portion of radiation that is emitted by infrared radiation source 14 to infrared detector 16. Thus, an intensity of the radiation that is emitted by infrared radiation source 14 may be monitored. Optics 18 may include a shutter or other component that is configured to block radiation (e.g., that is emitted by infrared radiation source 14) from reaching infrared detector 16. When the radiation is blocked, a baseline measurement may be made (e.g., a dark current or a detection level that is due to stray radiation).

Infrared detector 16 may be configured to detect SWIR radiation from tissue surface 22 that enters reflection measurement unit 12 via unit aperture 19. Infrared detector 16 may include one or more component detectors. For example, radiation that is reflected by tissue surface 22 may be enabled to impinge on a component detector of infrared detector 16 via one of component apertures 40.

Two or more different component radiation detectors may be configured to detect, or be optimized to detect, SWIR radiation in one or more spectral bands. A component detector may include a solid state or other photoelectric transducer or photodetector that is configured or optimized for one or more spectral bands of SWIR radiation. A component detector may include a thermal detector, a photon detector (e.g., including InGaAS), or another type of wideband detector. The temperature of a component detect of infrared detector 16 may be regulated (e.g., via thermoelectric cooling or heating) or may be unregulated.

Infrared detector 16 or controller 28 may include an amplifier to amplify a detection signal that is produced by infrared detector 16. For example, the amplifier may include a trans-impedance amplifier or other amplifier.

Infrared detector 16 or controller 28 may include a logarithmic converter that enables direct calculation of an absorbance value of the tissue, or of a quantity that is proportional to an absorbance. The absorbance data may be used to analyze a liquid, such as water or blood, below tissue surface 22 (e.g., detect a pressure ulcer or a concentration of a drug or other substance in the blood).

Component apertures 40 may be arranged such that radiation in a particular wavelength band that is emitted by a particular component infrared source of infrared radiation source 14 and that is reflected by tissue surface 22 is likely to impinge on a corresponding (e.g., configured or optimized to detect radiation in that same wavelength band) component detector of infrared detector 16. For example, the positions of a pair of corresponding component apertures 40 may be arranged such that radiation that irradiates tissue surface 22 via one of the corresponding component apertures 40 may be specularly reflected by tissue surface 22 into the other of the pair of corresponding component apertures 40.

Unit aperture 19 of optical head 13 may be configured to be placed against or near tissue surface 22. Optical head 13 may be provided with a removable protective cover 20 that may be placed over unit aperture 19 when reflection measurement unit 12 is in use. At least an outer surface of removable protective cover 20 may be constructed of materials that are suitable (e.g., approved by an appropriate organization) for contact with human skin or other tissue surfaces. At least a region of protective cover 20 (e.g., a region that is configured for placement over unit aperture 19) is substantially transparent or translucent in the spectral bands in which reflection measurement unit 12 is configured to operate. Suitable materials may include, for example, rigid vinyl, polycarbonate, POLY IR® plastic materials, or other materials such as poly urethane (PU)b, thermoplastic elastomers (TPE), silicones (LSR) and the like.

Removable protective cover 20 may include a structure (e.g., tab, projection, notch, clip, or other structure) that cooperates with corresponding structure on optical head 13 to prevent or inhibit removable protective cover 20 from accidentally or unintentionally falling off of optical head 13, e.g., during use.

Protective cover 20 may be disposable, cleanable, or sterilizable. Removable protective cover 20 may be removed from optical head 13 and replaced (e.g., with a different removable protective cover 20, or with the same removable protective cover 20 after cleaning and sterilization) between uses of reflection measurement unit 12 on different patients. Use of removable protective cover 20 may enable sanitary use of reflection measurement unit 12 on different patients while not exposing reflection measurement unit 12 from repeated cleaning or sterilization.

Liquid analysis system 10 may include a controller 28. Controller 28 may include a microcontroller unit (MCU), or one or more other types of controller, microprocessor or processor. Controller 28 may include for example two or more intercommunicating devices or units. Controller 28 may be configured to control operation of infrared radiation source 14, and to receive signals that are indicative of detected radiation from infrared detector 16. For example, controller 28 may include circuitry that is configured to control operation of infrared radiation source 14 and infrared detector 16. Controller 28 may be configured to operate in response to operation of user controls 27. For example, user controls 27 may include one or more user touch-operable controls, such as pushbuttons, dials, switches, levers, touch-sensitive surfaces, or other touch-operable controls. User controls 27 may include other types of controls, such as light-sensitive controls, sound-operated controls, electromagnetically-operable controls, proximity sensors, pressure sensors, or other types of controls.

Controller 28 may be configured to dynamically adjust the intensity of radiation that is emitted by infrared radiation source 14, e.g., in accordance with intensities that are detected by infrared detector 16. For example, the intensity may be adjusted to accommodate various tissue thicknesses, skin coloration, or other characteristics. The intensities of a component infrared source may be adjusted in accordance with output of another component infrared source.

Controller 28 may be configured to digitally filter the signals of infrared detector 16, e.g., to remove effects of baseline wandering and artifacts caused by patient movement.

Controller 28 may include a processor or processing units that may be configured to operate in accordance with programmed instructions. Controller 28 or a processor of controller 28 may communicate with an external device 30 via connection 36. External processing device 30 may represent a device with processing capability, such as a computer, smartphone, or other device. External processing device 30 may be portable (e.g., a portable computer or smartphone) or may be fixed (e.g., a server). External processing device 30 may include or communicate with an input device 34 (e.g., keyboard, keypad, touch screen, pointing device, or other input device), an output device 32 (e.g., display screen or other output device), or both. Connection 36 may represent a wire or cable connection, a wireless connection (e.g., Bluetooth), a network connection, or another communications connection.

External processing device 30 may be utilized to communicate commands or programmed instructions to control operation of controller 28. For example, external processing device 30 may be operated using input device 34 to download parameters or instructions (e.g., a measurement protocol) to controller 28. Measured results from operation of reflection measurement unit 12, or results of analysis of the measured results, preformed by, for example, external processing device's processor 38, may be output by output device 32 of external processing device 30 for examination or review by a user of liquid analysis system 10.

External processing device 30 may communicate (e.g., via a network such as the Internet) with one or more other processors, computers, or servers. For example, measure spectral reflection or transmission data may be communicated to a remote server. The remote server may analyzed the transmitted data and return a diagnosis or other indication of a state of a medical condition.

Controller 28 may communicate with memory 24 (and/or external processing device's memory 39). Memory 24 may include one or more volatile or nonvolatile memory devices. Memory 24 may be incorporated within reflection measurement unit 12, external processing device 30, or elsewhere. Memory 24 may be utilized to store, for example, programmed instructions for operation of controller 28, data or parameters for use by controller 28 during operation, or results of operation of controller 28.

Controller 28 and or processor 38 may communicate with data storage device 26. Data storage device 26 may include one or more fixed or removable nonvolatile data storage devices. Data storage device 26 may be incorporated within reflection measurement unit 12, external processing device 30, or elsewhere. For example, data storage device 26 may include a computer readable medium for storing program instructions for operation of processing unit of controller 28 or of external processing device 30. It is noted that data storage device 26 may be remote from the processing unit. In such cases data storage device 26 may be a storage device of a remote server storing an installation package or packages that can be downloaded and installed for execution by the processing unit. Data storage device 26 may be utilized to store data or parameters for use by controller 28 during operation or results of operation of controller 28 (e.g., detection of radiation).

Data storage device 26 may be used to store data that relates spectral absorption, transmission, or reflection characteristics of tissue surface 22 to one or more medical conditions. The data may be stored in the form of a database. Processor or controller 28, or another processor or controller may be configured to carry out methods as described herein.

In accordance with an embodiment of the present invention, a system for noninvasive analysis of subcutaneous liquids may be based on measured transmission of SWIR radiation.

FIG. 2A is a schematic drawing of a measurement unit of a system for noninvasive analysis of subcutaneous liquids based on transmission of infrared radiation, in accordance with an embodiment of the present invention.

Transmission measurement unit 50 may be used in a system for noninvasive analysis of subcutaneous liquids, such as in liquid analysis system 10 (e.g., in place of, or in addition to, reflection measurement unit 12 of FIG. 1A). Transmission measurement unit 50 is configured to measure transmission through a body part 52. For example, body part 52 may represent a part of the body (e.g., ear, finger, fold of skin) through which a measurable fraction of SWIR radiation is transmitted.

Transmission measurement unit 50 includes radiation source arm 54 and detection arm 55.

Radiation source arm 54 may include infrared radiation source 14 and source optics 53*a*. In some cases, infrared radiation source 14 may be located outside of radiation source arm 54. In such a case, source optics 53*a* may be configured (e.g., with a mirror, light pipe, or optical fiber) to convey radiation from infrared radiation source 14 to source arm aperture 57*a*.

As described above, infrared radiation source 14 may include two or more separate component infrared sources. Source optics 53*a* may be configured to convey radiation from the component infrared sources, concurrently or sequentially, to source arm aperture 57*a*, or to separate component apertures of source arm aperture 57*a*.

Source optics 53*a* may be or may include a dispersive element (e.g., grating, prism, element with spectrally selective optical layers or coating, or another dispersive element), focusing optics, and a micro-mirror array for directing radiation of one or more selected wavelengths of radiation from infrared radiation source 14 toward source arm aperture 57*a*.

Detection arm 55 may include infrared detector 16 and detector optics 53*b*. In some cases, infrared detector 16 may be located outside of detection arm 55. In such a case, detector optics 53*b* may be configured (e.g., with a mirror, light pipe, or optical fiber) to convey radiation from detection arm aperture 57*b* to infrared detector 16.

As described above, infrared detector 16 may include two or more separate component detectors. Detector optics 53*b* may be configured to convey radiation from detection arm aperture 57*b*, concurrently or sequentially, to component detectors of infrared detector 16, or from separate component apertures of detection arm aperture 57*b* to component detectors of infrared radiation detector 16.

Detector optics 53*b* may include a dispersive element (e.g., grating, prism, element with spectrally selective optical layers or coating, or another dispersive element), focusing optics, and a micro-mirror array for directing radiation of one or more selected wavelengths of radiation from detector arm aperture 57*b* toward infrared detector 16.

Radiation source arm 54, detection arm 55, or both, may be rotated outward (away from one another) or inward (toward one another). Outward rotation of radiation source arm 54 or detection arm 55 may enable insertion of body part 52 between the arms. Inward rotation of radiation source arm 54 or detection arm 55 may bring source arm aperture 57*a* and detection arm aperture 57*b* into contact with or near to body part 52. Source arm aperture 57*a* and detection arm aperture 57*b* may each be covered with a removable protective cover 20.

A rotation mechanism 56 may be configured to enable the outward or inward rotation of radiation source arm 54 and detection arm 55. For example, rotation mechanism 56 may include a hinge, gimbal, bearing, or other mechanism to enable rotation of radiation source arm 54 or detection arm 55. For example, a separate rotation mechanism 56 for one of radiation source arm 54 and detection arm 55. Separate rotation mechanisms 56 may be provided for both radiation source arm 54 and detection arm 55 (e.g., as shown schematically in FIG. 2A). A single rotation mechanism 56 may be provided (e.g., a single hinge mechanism) between radiation source arm 54 and detection arm 55 (e.g., as shown schematically in FIGS. 2B and 2C). Rotation mechanism 56 may include a spring, latch, or other mechanism to hold radiation source arm 54 and detection arm 55 against body part 52 when body part 52 is inserted between radiation source arm 54 and detection arm 55. Thus, rotation mechanism 56 may attach transmission measurement unit 50 to body part 52.

Rotation mechanism 56 may be configured to enable measurement of a thickness of body part 52. For example, rotation mechanism may include an encoder or other measuring device for measuring an angle of rotation of rotation mechanism 56. Alternatively or in addition, rotation mechanism may include an angular scale or mechanical rotation gauge for determining an angle of rotation of rotation mechanism 56. A measured rotation angle, together with a known distance from (e.g., and axis of rotation of) rotation mechanism 56 from source arm aperture 57*a* or from detection arm aperture 57*b* may be used (e.g., by a processor or controller) to calculate the thickness.

When source arm aperture 57*a* and detection arm aperture 57*b* are positioned on or near body part 52, transmission measurement unit 50 may be operated to measure of transmission of SWIR radiation from infrared radiation source 14 through body part 52 to infrared detector 16.

FIG. 2B schematically illustrates attachment of the measurement unit of FIG. 2A to a finger.

For example, transmission measurement unit 50 may be clipped to finger tip 60 to measure transmission of SWIR radiation through finger tip 60. For example, the transmission measurement may be indicative of a medical condition, such as the concentration of a substance in blood that flows through finger tip 60.

FIG. 2C schematically illustrates attachment of the measurement unit of FIG. 2A to an ear.

For example, transmission measurement unit 50 may be clipped to outer ear 62 to measure transmission of SWIR radiation through outer ear 62. For example, the transmission measurement may be indicative of a medical condition, such as the concentration of a substance in blood that flows through outer ear 62.

In accordance with an embodiment of the present invention, a reflection or transmission measurement may be utilized to characterize tissue in a patient.

A spectral reflectance measurement $R(\lambda)$ may be expressed as $$R(\lambda) = \frac{I(\lambda) - B_0(\lambda)}{I_0(\lambda) - B_0(\lambda)}$$

where $I_0(\lambda)$ is a measured source intensity, $I(\lambda)$ is a measured reflected intensity, and $B_0(\lambda)$ is a baseline measurement (e.g., measured when infrared radiation source 14 is turned off or when infrared detector 16 is covered, e.g., by a shutter). Source intensity $I_0(\lambda)$ may be monitored continuously (e.g., by a dedicated detector), or may be measured in the absence of tissue (e.g., a skin surface or body part) in the optical path from infrared radiation source 14 to infrared detector 16.

In some cases, baseline measurement $B_0(\lambda)$ may be ignored when $B_0(\lambda)$ is much smaller than $I_0(\lambda)$ or $I(\lambda)$.

The relative spectral absorbance $A(\lambda)$, which may be used to characterize the tissue, may be calculated by:

$$A(\lambda) = -\log\left[\frac{R(\lambda)}{\alpha_R}\right] \sim -\log\left[\frac{I(\lambda)}{\alpha_R I_0(\lambda)}\right]_{I, I_0 \gg B_0}$$

where the dimensionless value $A(\lambda) = \alpha_A L$ is the relative spectral absorbance, $\alpha_A$ is the absorption coefficient, L is the path-length or tissue penetration depth; and $\alpha_R$ is the reflection coefficient. In general, the relative absorbance $A(\lambda)$ corresponds to spectral extinction, which results from both absorption and scattering.

Reflectance measurements in two or more spectral bands, $\Delta\lambda_i$ may be performed on a single region of skin or tissue to yield separate measured values of $A(\Delta\lambda_j)$ or $R(\Delta\lambda i)$. For example, the spectral bands may include two or more of the wavelength ranges ~1400 nm-1500 nm (strongly absorbed by water), ~1000 nm-1350 nm (no strong absorption by water), and ~1500 nm-2100 nm (no strong absorption by water).

The differential absorption $A_{Diff}$ may be calculated from measurements in two wavelength bands, $\Delta\lambda_i$ and $\Delta\lambda_j$, where $i \neq j$:

$$A_{Diff} = A(\Delta\lambda_i) - A_{ref}(\Delta\lambda_j) \sim \log[R(\Delta\lambda_i)] - \log[\Delta R_{ref}(\lambda_j)] \sim \log\left[\frac{R(\Delta\lambda_i)}{R_{ref}(\Delta\lambda_j)}\right].$$

$A_{ref}$ and $R_{ref}$ refer the absorbance and reflectance in one of the spectral bands that serves as a reference band. For example, radiation in the reference band may be largely absorbed, scattered, or transmitted whether or not a medical condition to be detected is present. For example, the wavelength range of ~1400 nm-1500 nm (strong water absorption), a portion of this range, or another similarly unaffected spectral range may be selected as the reference band.

Absorption, scattering, or transmission of radiation in one of the other spectral bands, referred to as the operating band, may be detectibly dependent on the presence of absence of the medical condition. For example, the operating band may include one or both of the spectral ranges ~1000 nm-1350 nm, ~1550 nm-2100 nm, one or more portions of one or both spectral ranges, or another suitable spectral range. Here, and throughout the specification, the symbol ~ indicates an approximation (e.g., ±10%).

The differential absorption may be related to the state of the tissue (e.g., presence, absence, degree, or other state of a medical condition). For example, a database of previous measurement results may associate a value of a differential absorption with a state of a medical condition such as inflammation (e.g., otitis media, or other inflammation), tumor (e.g., in the colon, or elsewhere), or other conditions. The differential absorption value may be used to differentiate between conditions (e.g., inflammation and tumor, healthy and diseased tissue), detect or measure liquid within tissue, or other conditions.

In some cases, reflection measurements may be made on a region of a tissue surface when the underlying tissue is expected to be healthy (e.g., based on other medical indications), and another where presence of unhealthy tissue is suspected.

The differential absorption $A_{Diff}$ of two measurements with the same setup and in the same wave-band $\Delta\lambda_i$, i=1, 2, 3 yield two different spectral absorbance values, $A_{ref}(\Delta\lambda)$ and $A_{SUS}(\Delta\lambda)$, which correspond to healthy tissue (reference absorbance, $A_{ref}$) and suspicious tissue $A_{SUS}$, respectively:

$$A_{Diff} = A_{SUS}(\Delta\lambda_i) - A_{ref}(\Delta\lambda_i) \sim$$
$$\log[R_{SUS}(\Delta\lambda_i)] - \log[R_{ref}(\Delta\lambda_i)] \sim \log\left[\frac{R_{SUS}(\Delta\lambda_i)}{R_{ref}(\Delta\lambda_i)}\right].$$

To improve detectability, all three spectral ranges $\Delta\lambda_i$ i=1, 2, 3 can be used simultaneously.

In some cases, chromophore content may be measured quantitatively. In some cases, differentiation is limited to two states, e.g., healthy or diseased (e.g., presence of pressure ulcer indicated by accumulation of subcutaneous liquid in the) tissue.

In some cases, a state of a medical condition (e.g., presence of diseased tissue) may be determined by calculating the tissue liquid index (TLI), the sub-dermal fluid index (SDFI), or another quantity. A parameter C, such as TLI, SDFI, or another parameter, can be defined as a normalized difference of the reflectance as measured at two different wavelength bands $\Delta\lambda_i$ and $\Delta\lambda_j$, where i≠j:

$$C = \frac{R(\Delta\lambda_i) - R(\Delta\lambda_j)}{R(\Delta\lambda_i) + R(\Delta\lambda_j)}$$

In some cases, C may be approximated by $$C = \frac{R(\Delta\lambda_i) - R(\Delta\lambda_j)}{R(\Delta\lambda_j)} \text{ or}$$
$$C = \frac{R(\Delta\lambda_i)}{R(\Delta\lambda_i) + R(\Delta\lambda_j)} \text{ or}$$
$$C = \text{slope}[R(\Delta\lambda)]$$

Figure 3:
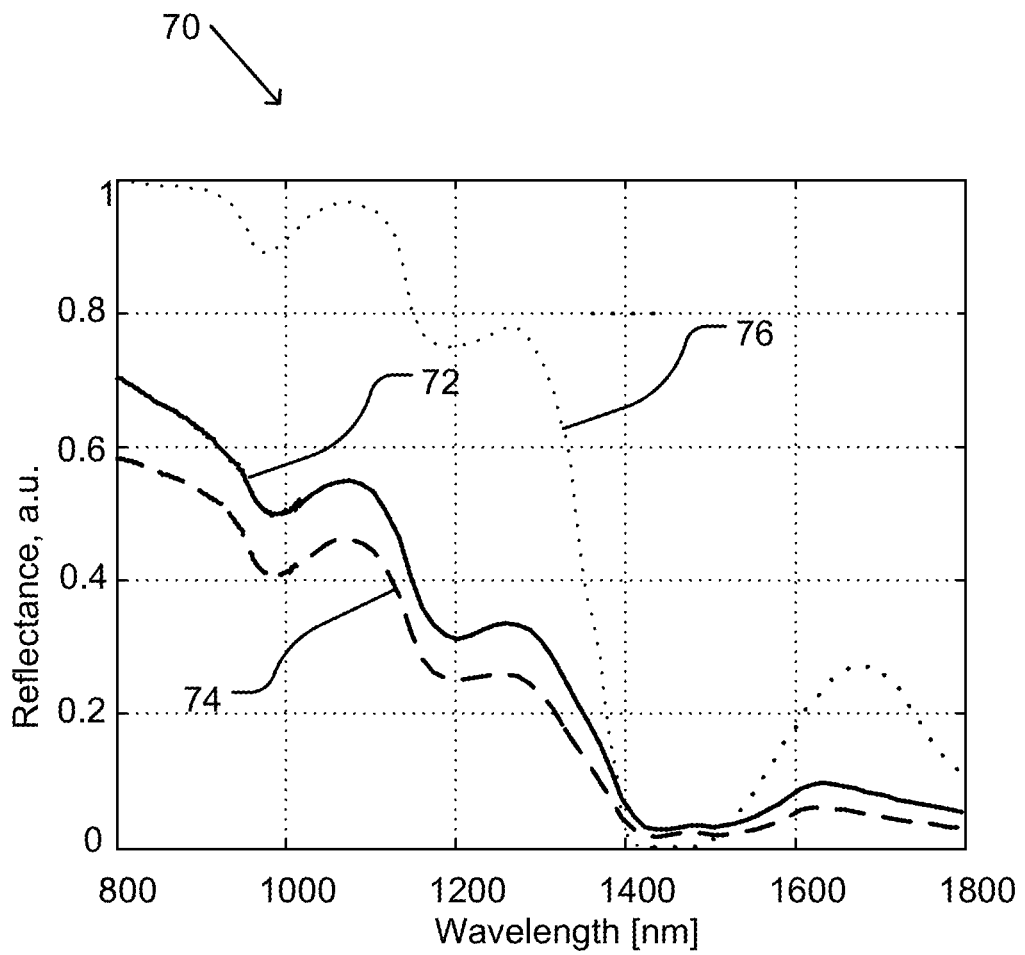
FIG. 3 shows an example of a graph of spectral reflectance.

FIG. 3 shows an example of a graph of spectral reflectance.

Graph 70 shows measured reflectance in arbitrary units as a function of wavelength. Normal tissue curve 72 may represent spectral reflectance for normal, or healthy, tissue. Diseased tissue curve 74 may represent spectral reflectance for diseased, or unhealthy, tissue. Water curve 76 represents spectral transmittance for water (e.g., for a particular optical path such as 1 mm; transmittance=1−absorbance) in arbitrary units.

It may be noted that in the wavelength band of 1400 nm-1500 nm (low water reflectance due to strong absorption of radiation), there is little difference between normal tissue curve 72 and diseased tissue curve 74. However, in the adjacent bands (e.g., wavelength less than about 1350 nm), the difference is more pronounced.

Quantification of chromophores may enable estimation of changes in concentration levels of substances or materials (e.g., drugs, or other substances) that may be administrated by injection, infusion, or otherwise.

The spectral transmittance of blood $T_B$ may be expressed as $$T_B(\lambda) = I(\lambda)/I_0(\lambda) = e^{-(\alpha_B(\lambda) + \alpha(\lambda)) \cdot L}$$

where $\alpha_B(\lambda)$ represents the absorption coefficient of blood and (e.g., in units of cm$^{-1}$), respectively, at wavelength $\lambda$, $\alpha(\lambda)$ is the absorption coefficient of additional components of the tissue, and L is the length of the absorbing path (e.g., in cm). $I(\lambda)$ is the detected intensity of transmitted radiation, and $I_0(\lambda)$ is the intensity of incident radiation.

Similarly, $T_{\% S}$, the spectral transmittance of a mixture of blood and an introduced substance may be expressed as $$T_{\% S}(\lambda) = I(\lambda)/I_0(\lambda) = e^{-(\alpha_S(\lambda) + \alpha_B(\lambda) + \alpha(\lambda)) \cdot L}$$

where $\alpha_S(\lambda)$ represents the absorption coefficient of the introduced substance.

The absorption coefficients may relate to the concentrations of blood $C_B$ and of the introduced substance $C_S$:

$$a_B(\lambda) = \varepsilon_B(\lambda) \cdot C_B, \text{ and}$$

$$\alpha_S(\lambda) = \varepsilon_S(\lambda) \cdot C_S.$$

where $\varepsilon_B$ and $\varepsilon_S$ represent the absorptivity coefficients of blood and of the introduced substance (e.g., in units of 1·mol$^{-1}$·cm$^{-1}$ or 1·g$^{-1}$·cm$^{-1}$; also referred to as the specific absorption coefficient or mass absorption coefficient), respectively.

The relative absorbance $A_S$ (dimensionless) at wavelength $\lambda$ may be related to the concentration of introduced substance:

$$A_S(\lambda, C_S) = \log\left(\frac{T_{\% S}}{T_B}\right) = (\varepsilon_S(\lambda) \cdot C_S + \alpha(\lambda)) \cdot L.$$

The relative absorbance may be expressed as a linear equation:

$$A_S = p_1 \cdot C_S + p_2$$

with coefficient $p_1$ (e.g. in 1·g$^{-1}$) and $p_2$ (dimensionless).

The normalized spectral transmittance S at a wavelength $\lambda_n$ may be calculated from a measurement k as:

$$S(\lambda_n, k) = \frac{I_{meas}(\lambda_n, k) - I_{dark}(\lambda_n)}{I_{ref}(\lambda_n, k_0) - I_{dark}(\lambda_n)}$$

$I_{meas}(\lambda_n, k)$ is a measured radiation intensity at wavelength $\lambda_n$ for measurement k, $I_{meas}(\lambda_n, k)$ being proportional to $T_{\% S}$. $I_{ref}(\lambda_n, k_0)$ is a reference signal for a measurement $k_0$ made prior to introduction of the substance into the blood, $I_{ref}(\lambda_n, k_0)$ being proportional to $T_B$. $I_{dark}(\lambda_n)$ represents a baseline measurement that is made in the absence of a radiation source, e.g., when the radiation source is switched off.

The differential spectral absorbance $A_{Diff}$ for measurement k at two wavelengths $\lambda_1$ and $\lambda_2$ may thus be calculated as $$A_{Diff}(\lambda_1, \lambda_2) = A(\lambda_1) - A(\lambda_2) = \log[S(\lambda_1, k)] - \log[S(\lambda_2, k)] = \log\left[\frac{S(\lambda_1, k)}{S(\lambda_2, k)}\right]$$

For example, $T_B$ and $T_{\%\,S}$ may represent relative spectral transmittances of blood and of a mixture of blood and a introduced substance measured at two wavelengths $\lambda_1$ and $\lambda_2$:

$$T_B = \frac{T(\lambda_1)}{T(\lambda_2)} = e^{-(K_B + \alpha) \cdot L},$$

$$T_{\%S} = \frac{T(\lambda_1)}{T(\lambda_2)} = e^{-(K_S + K_B + \alpha) \cdot L}.$$

$K_B = (a_B(\lambda_2) - a_B(\lambda_1))$ and $K_S = (a_S(\lambda_2) - a_S(\lambda_1))$ represent the differential absorption coefficients of blood and of the introduced substance, respectively.

The relative differential absorbance $A_S$ (dimensionless) at two wavelengths $\lambda_1$ and $\lambda_2$ is related to the concentration of introduced substance as:

$$A_S(\lambda_1, \lambda_2, C_S) = \log\left(\frac{T_{\%S}}{T_B}\right) = ((\varepsilon_S(\lambda_1) - \varepsilon_S(\lambda_2)) \cdot C_S + \alpha(\lambda)) \cdot L$$

The normalized spectral transmittance S at two wavelengths $\lambda_1$ and $\lambda_2$ may be calculated from measurement k as:

$$S(\lambda_1, \lambda_2, k) = \frac{[I_{meas}(\lambda_1, k) - I_{dark}(\lambda_1)]/[I_{meas}(\lambda_2, k) - I_{dark}(\lambda_2)]}{[I_{ref}(\lambda_1, k_0) - I_{dark}(\lambda_1)]/[I_{ref}(\lambda_2, k_0) - I_{dark}(\lambda_2)]}$$

The differential spectral absorbance $A_{Diff}$ for measurement k at two wavelengths $\lambda_1$ and $\lambda_2$, then is:

$$A_{Diff}(\lambda_1, \lambda_2) = \log[S(\lambda_1, \lambda_2, k)]$$

The differential spectral absorbance measurement may eliminate the effects of background materials. For example, if the absorption and scattering by the background materials (e.g., tissue components other than water, or a substance that is introduced into the blood) are substantially constant in both measured spectral bands, than the differential spectral absorbance may be indicative of the water content of the tissue (e.g., as indicative of the presence or absence of a medical condition in which fluids accumulate in the tissue, or indicative of water content of blood).

A known relationship between the differential spectral absorbance and a concentration of the substance in the blood may be applied to the measured differential spectral absorbance to determine a concentration of the substance in the blood. For example, the known relationship be applied as a parameterized formula expressing the relationship (e.g., a polynomial or other formula), as a lookup table, or in another manner.

Figure 4:
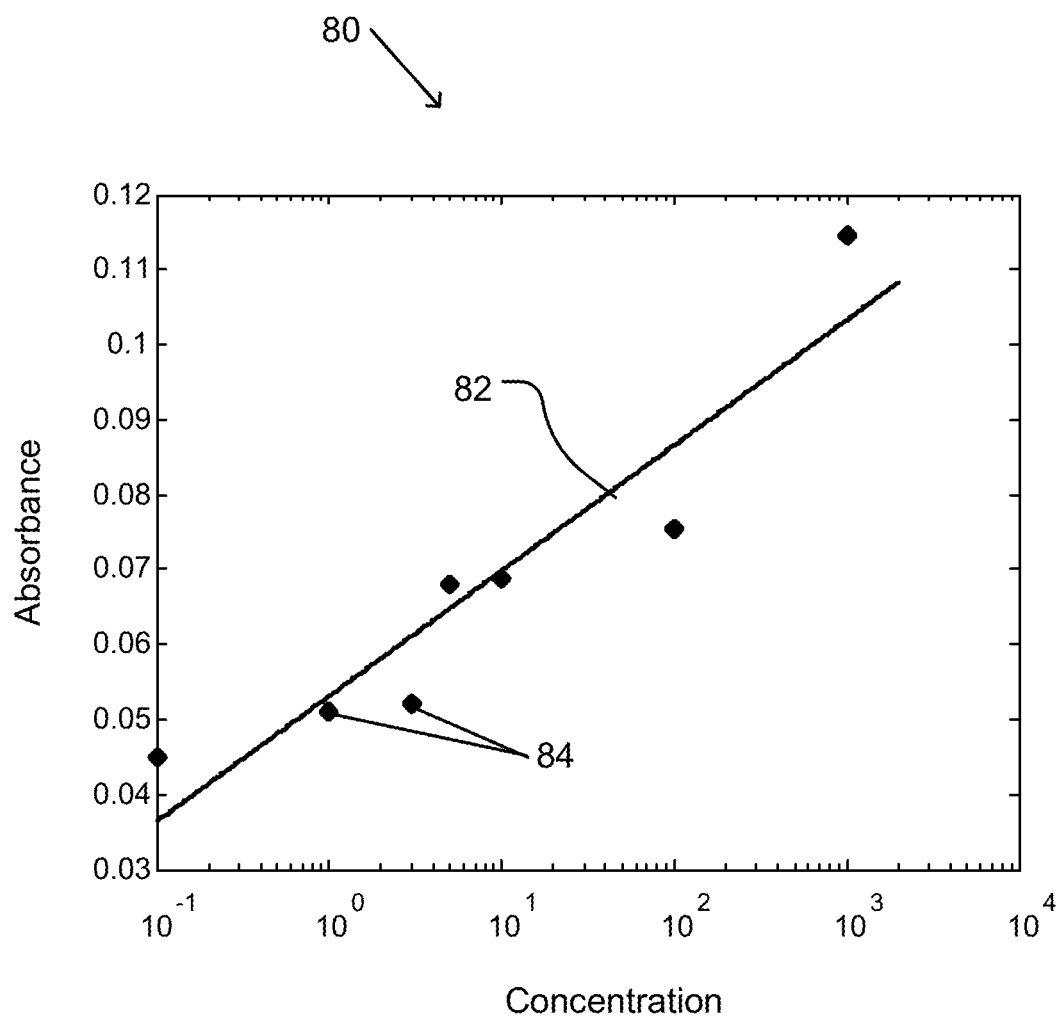
FIG. 4 shows a graph of an example of a relationship of absorbance to concentration of a substance.

FIG. 4 shows a graph of an example of a relationship of absorbance to concentration of a substance.

Line 82 of graph 80 shows a relationship between a relative absorbance (dimensionless) and the concentration of a substance (e.g., propofol) in blood, as plotted on a logarithmic scale (e.g., in units of µg/ml). The relationship may be derived from laboratory measurements 84, e.g., from transmission measurements on cuvettes containing various concentrations of the substance in blood. A relationship may be derived by application of a fitting technique to fit line 82 to laboratory measurements 84.

Figure 5:
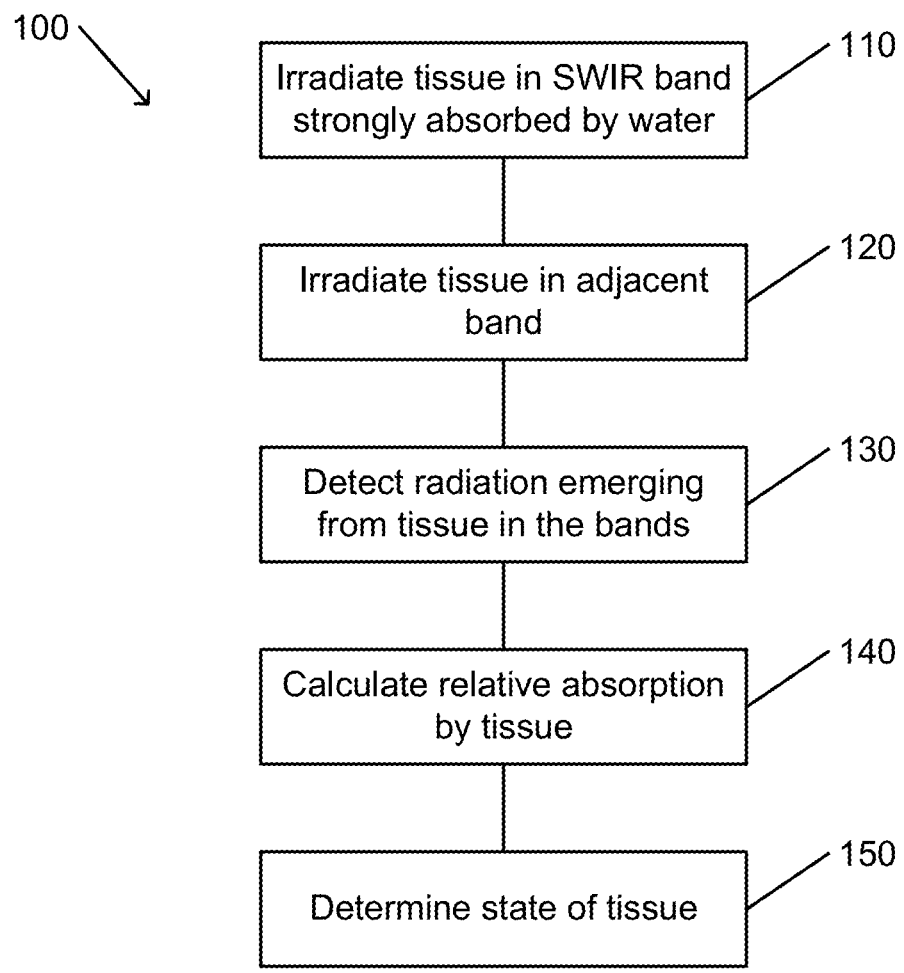
FIG. 5 is a flowchart depicting a method for noninvasive analysis of subcutaneous liquids, in accordance with an embodiment of the present invention.

FIG. 5 is a flowchart depicting a method for noninvasive analysis of subcutaneous liquids, in accordance with an embodiment of the present invention.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Operations of subcutaneous liquid analysis method 100 may be executed by a processor of a controller of a device for subcutaneous liquid analysis, or by a processor that is in communication with a controller of a device for subcutaneous liquid analysis.

Execution of subcutaneous liquid analysis method 100 may be initiated by a user of a device for subcutaneous liquid analysis. For example, a user may operate a control to initiate execution of subcutaneous liquid analysis method 100. As another example, execution of subcutaneous liquid analysis method 100 may be initiated automatically when a device for subcutaneous liquid analysis is activated (e.g., turned on), and when it is detected (e.g., by an optical sensor or by a proximity sensor) that one or more apertures of the device are in contact with a tissue surface.

The tissue may be irradiated with SWIR radiation in a spectral band that is strongly absorbed by water (block 110). For example, a tissue surface may be irradiated with SWIR radiation in the wavelength range from about 1400 nm to about 1500 nm. The radiation may originate from a wideband source (e.g., an incandescent or other thermal source, or from a fluorescent source), or from a narrowband source (e.g., laser diode or light emitting diode). The irradiation may be filtered or otherwise manipulated. For example, radiation that is emitted by a wideband radiation source may be filtered or otherwise manipulated to select only that radiation that is within the water-absorbed spectral band.

The tissue may be irradiated with SWIR radiation in a spectral band that is adjacent to the water-absorbed spectral band (block 120). For example, a gap between the adjacent spectral band and the water-absorbed spectral band may be no more than 200 nm. In some cases, the gap may be no more than 100 nm. A single wideband source may produce both the radiation in the water-absorbed spectral band and in the adjacent spectral band. In some cases, the radiation in the adjacent spectral band may be isolated from radiation that is emitted by a wideband source prior to irradiation of the tissue.

Radiation that emerges from the tissue in each of the spectral bands may be detected (block 130). The detector is configured to produce a signal that is indicative of an intensity of the emerging radiation.

For example, one or more detectors may be configured to detect radiation that emerges from the tissue surface that is irradiated. For example, optics of the radiation source and the radiation detector may be aimed at a single tissue surface. In this case, the detector is configured to measure backscattered or reflected radiation. As another example, the detector may be configured to detect radiation that emerges from a tissue surface on the opposite side of the tissue from the tissue surface that is irradiated. In this case, the detector is configured to measure radiation that is transmitted by the tissue.

In some cases, different detectors may be configured to measure emerging radiation in each of the wavelength bands. For example, each detector may be constructed of a material that produces an electric signal only when irradiated with radiation in one of the spectral bands. As another example, detector optics (e.g., including a filter or grating) may restrict radiation that is outside of that spectral band from irradiating the detector. In some cases, the detector may be configured to detect radiation in both spectral bands. In this case, separate measurement of the emerging radiation in the different spectral bands may be effected by separate (e.g., sequential or alternating) irradiation of the tissue with radiation in each of the spectral bands.

In some embodiments, emerging radiation may be measured at different distances from a location of the irradiation. For example, emerging radiation may be measured concurrently by a plurality of detectors that are arranged at different distances from a location on the tissue surface that is irradiated. As another example, emerging radiation may be measured sequentially in time at different distances by one or more detectors whose distance from the location of irradiation may be changed (e.g., automatically or manually). In this case, a detector may be provided with a sensor or mechanism (e.g., encoder or other sensor or mechanism) that is configured to measure a distance between a detector and the radiation source. In some embodiments, signals received from each detector may correspond to the distance of the detector from the light source. In some embodiments, the shape and/or intensity of a signal received by a detector may correspond to a medical condition in the tissue, for example shape of a signal changed in measurements for healthy tissue and for deep tissue injury, so that the shape of the signal received for a healthy tissue changes when measuring an injured tissue of the same subject (e.g., person). The shape of a signal may change because of different types of chromophores and different types of chemical functional groups on a chromophore. For example a phenol ring on a chromophore will have different absorption graph shape in comparison to a CO chemical bond, CH chemical bond, or CN chemical bond. Absorption graph different shape means different location of the absorption peak or peaks in different wavelengths and at different peak heights (amplitudes). In some embodiments, a plurality of detectors may be used, each of the plurality of detectors may have a different distance from the radiation source. It should be appreciated that the signal received by each detector may have different amplitudes. According to some embodiments, the processor or controller may combine the readings of the plurality of detectors and calculate the slope of the combined absorption graph (e.g., a graph that represents the result of combining all detected amplitudes). A change in the state of the tissue may be determined, according to some embodiments, when a change in the slope of the combined absorption graph is detected (e.g., by processor 38 and/or controller 28 in FIG. 1).

Detection of the emerging radiation may be preceded by, followed by, or may be concurrent with one or more calibration, baseline, or reference measurements. For example, a baseline or dark measurement may be made when the radiation source is not being operated. The baseline measurement may determine a signal that is produced by the detector (e.g., due to detector electronics or to stray radiation impinging on the detector surface) when no radiation of interest is present. A calibration measurement may be made when radiation that is emitted by the source is directly (e.g., not via tissue) conveyed to the detector. Such a calibration measurement, when made concurrently with, or immediately prior to or after, the measurement of emerging radiation may enable compensation for drifting in source intensity or detector sensibility. In some cases, a reference measurement may be made on the radiation that emerges from the tissue under known conditions (e.g., on a skin surface that is known to overlie healthy tissue, or prior to introduction of a substance into the blood).

The measurements of emerging radiation may be used to calculate a relative absorption by the tissue (block 140).

For example, a relative reflectance may be calculated by calculating a ratio of a measured intensity of reflected (e.g., due to backscattering) radiation in one of the spectral bands to the measured intensity of reflected radiation in another spectral band. A relative absorption may be inferred from the relative reflectance, e.g., on the assumption that a characteristic penetration depth of the radiation is the same in both spectral bands. If the characteristic penetration depth of the radiation is known (e.g., from laboratory experiments), a differential absorbance may be calculated.

A relative transmission may be calculated by calculating a ratio of a measured intensity of transmitted radiation in one of the spectral bands to the measured intensity of transmitted radiation in another spectral band. Since the path length through the tissue is the same for both spectral bands, a relative absorption may be inferred from the relative transmission. If the thickness of the tissue (L) is known (or may be estimated) and constant, a differential absorbance of the tissue may be calculated.

The relative differential absorbance $A_S$ (dimensionless) at two wavelengths $\lambda_1$ and $\lambda_2$ is related to the concentration of introduced substance as:

$$A_S(\lambda_1, \lambda_2, C_S) = \log\left(\frac{T_{\%S}}{T_B}\right) = ((\varepsilon_S(\lambda_1) - \varepsilon_S(\lambda_2)) \cdot C_S + \alpha(\lambda)) \cdot L$$

According to some embodiments, Raman spectroscopy as described in further detail below, may be employed to analyze the measurement data, and determine changes in concentration of any chemical compound inside the tissue due to, for example, a deep tissue injury. The calculated relative absorption may be utilized to determine a state of the tissue (block 150). For example, a calculated differential absorbance, relative reflection, relative transmission, or other calculated value that is related to relative absorption may be compared to previously measured values. The previously measured values may relate to a particular body part, suspected medical condition, introduced substance, or may otherwise relate to a specific state that is being examined. The comparison may include substitution of the calculated value in a functional relationship, may be used to retrieve an indication of the state of the tissue from a lookup table, or may be otherwise utilized in determining a state of the tissue.

It should be noted that deep tissue injuries may include presence of liquids at depths larger than about 5 mm compared to a corresponding region of a healthy tissue (e.g., of a healthy patient). Furthermore, deep tissue injuries may include increasing concentration (over time) of substances that are products of ischemic processes (causing damage to the tissue) such as free fatty acids and/or glycerol which are the breakdown products of the fatty part of the tissue (triglyceride). In the blood stream (unlike other tissues) triglyceride may appear in the form of very low density lipoproteins (VLDL) while in other tissue the structure of triglyceride is maintained. Accumulation of other substances (e.g., protease or myoglobin) may also indicate presence of a deep tissue injury. Therefore, in order to determine a state of deep tissue injury, calibration may be initially performed to identify substances in tissue indicating such an injury. Using the calculated relative absorption a state of deep tissue injury may be therefore determined, as described above.

According to some embodiments, a reflectance measurement may include detecting reflected radiation at different lateral distances from a radiation source. In some embodiments, analysis of such reflectance measurements at different distances may indicate a depth within the tissue of a detected feature.

Figure 6A:
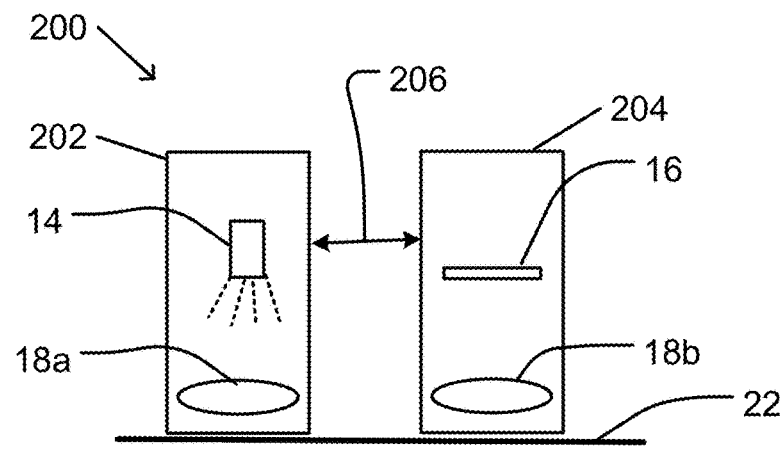
FIG. 6A schematically illustrates a system for measurement of reflection at a distance from a radiation source, in accordance with an embodiment of the present invention.

FIG. 6A schematically illustrates a system for measurement of reflection at a distance from a radiation source, in accordance with an embodiment of the present invention.

According to some embodiments, reflection measurement system 200 may include a source unit 202 and one or more detection units 204. Source unit 202 may include at least one infrared (IR) radiation source 14 and source optics 18a (e.g., lenses etc.) for directing a beam of radiation, e.g., into a tissue surface 22. Each detector unit 204 may include at least one IR detector 16 and detector optics 18b (e.g., lenses etc.) for directing radiation, for instance radiation emerging from tissue surface 22, toward infrared detector 16. Detector unit 204 may be located at a measurement distance 206 from source unit 202. For example, measurement distance 206 may correspond to a distance between a center of an aperture of source unit 202 to a center of detector unit 204, and/or another measurement that characterizes a lateral distance between source unit 202 and detector unit 204.

In some embodiments, at least one of detector unit 204 and source unit 202 (or assemblies that include a plurality of detector units 204 and/or source units 202) may be moveable relative to one another so as to change measurement distance 206. In this case, reflectance measurements at different measurement distances 206 may be measured sequentially in time. The distance 206 between detector unit 204 and source unit 202 at the time of a measurement may be determined with a dedicated mechanism and/or sensor. For example, detector unit 204 and source unit 202 may be mounted on a fixture that includes a mechanism for adjusting a distance therebetween. The fixture may include a telescoping rod, a bendable joint, or any other mechanism to adjust a distance between detector unit 204 and source unit 202 in a controllable manner. The fixture may include fixed stops at known distances between detector unit 204 and source unit 202. Alternatively or in addition, a sensor may be provided to measure a distance between detector unit 204 and source unit 202. For example, a telescoping rod or bendable joint may be provided with an encoder to measure relative movement between detector unit 204 and source unit 202.

As another example, a rangefinder sensor may directly measure a distance between detector unit 204 and source unit 202.

In some embodiments, at least one source unit 202 and at least one detector unit 204 may be combined in a single measurement unit to concurrently measure radiation that emerges from tissue surface 22 at different lateral distances from source unit 202.

Figure 6B:
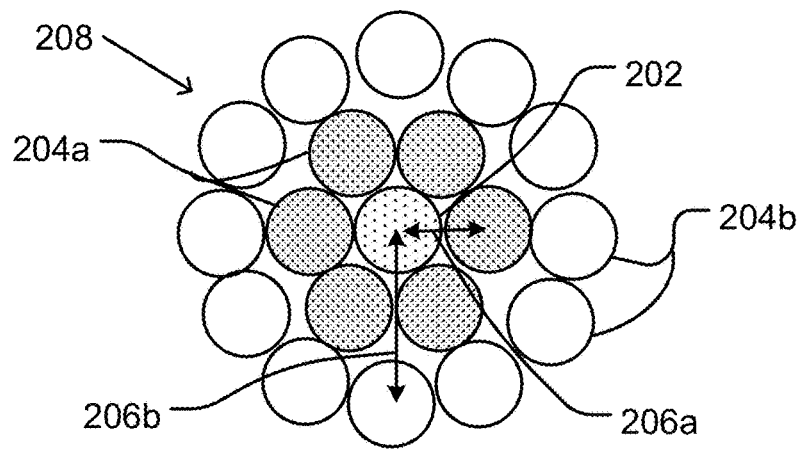
FIG. 6B schematically illustrates an arrangement of a measurement head for concurrent measurement of radiation that emerges from a surface at different lateral distances from the radiation source, in accordance with an embodiment of the present invention.

FIG. 6B schematically illustrates an arrangement of a measurement head for concurrent measurement of radiation that emerges from a surface at different lateral distances from the radiation source, in accordance with an embodiment of the present invention.

According to some embodiments, each measurement head 208 may include a single source unit 202 surrounded by a plurality of detector units 204 and separated by two different lateral distances form source unit 202. In the configuration shown in FIG. 6B, source unit 202 is surrounded by an arrangement of inner detector units 204a, each laterally separated from source unit 202 by a distance that is substantially equal to first distance 206a. Inner detector units 204a are surrounded by an arrangement of outer detector units 204b, each separated from source unit 202 by a lateral distance that is substantially equal to second distance 206b. In some embodiments, second distance 206b may be larger than first distance 206a.

It should be noted that the arrangement shown in FIG. 6B has been selected for illustrative purposes only. An actual arrangement may differ from the arrangement shown in FIG. 6B. For example, an arrangement may include detector units 204 at more than two distances from a source unit 202. An arrangement may include a different pattern of detector units and/or of source units. An arrangement may include more than one source unit 202. For example, different source units 202 may produce radiation with different wavelengths. A center unit may include a detector unit 204 (e.g., surrounded by sources 202).

In some embodiments, measurement of a distance to a detected feature may be advantageous. For example, measurement of a distance may enable differentiation between a superficial pressure ulcer and a deep ulcer. In some embodiments, such measurement of a distance may enable differentiation between a deep pressure injuries and superficial pressure ulcers. In some embodiments, a distance between the light source and the light sensor may be predetermined. In some embodiments, determination of such distance may allow determination of a medical condition in the tissue (e.g., deep tissue injury) due to changes in signal from a detector having a determined distance to the light source.

Pressure ulcers are areas of soft tissue breakdown that result from sustained mechanical loading of skin and underlying tissues. They can interfere with quality of life, activities of daily living, and rehabilitation and, in some cases, may be life threatening. Pressure ulcers can develop either superficially or deep within the tissues, depending on the nature of the surface loading and the tissue integrity. The superficial pressure ulcer type forms within the skin, with maceration and detachment of superficial skin layers. When allowed to progress, the damage may result in an easily detectable superficial ulcer.

In contrast, deep tissue ulcers arise in muscle layers covering bony prominences and are mainly caused by sustained compression of tissue. Deep tissue ulcers may develop at a faster rate than superficial ulcers, and result in more extensive ulceration with an uncertain prognosis.

In addition to absorption of radiation that traverses tissue, NIR and SWIR radiation may be strongly scattered by such tissue. The free scattering length may be in the range of about 0.3 mm to about 1 mm. In some embodiments, the scattering may be strongly forward peaked. Beyond a free transport scattering length (e.g., about 1 mm), directional correlation with the direction of the incident irradiation (the correlation between the actual direction and the direction of incidence) is lost such that radiation transport may be modeled as photon diffusion. In a photon diffusion model, scattering may be isotropic at locations that are more distant from radiation sources and boundaries than several times the free scattering length. Photons may follow complex trajectories that are considerably longer than the geometrical distance between the radiation source and the radiation detector.

Figure 7:
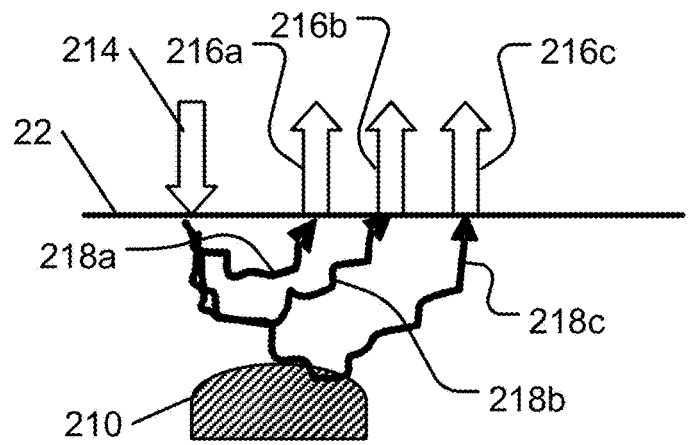
FIG. 7 schematically illustrates paths of incident radiation to different detector locations, in accordance with an embodiment of the present invention.

FIG. 7 schematically illustrates paths of incident radiation to different detector locations, in accordance with an embodiment of the present invention.

According to some embodiments, a deep lesion 210 (or other deep tissue injury) may be distant from tissue surface 22. Incident radiation 214 may enter tissue surface 22 (e.g., from a source unit 202 as shown in FIG. 6A). Emerging radiation 216a, 216b, and 216c may emerge from tissue surface 22 at different distances from incident radiation 214, having traversed radiation paths 218a, 218b, and 218c respectively within the tissue. It should be noted that as shown in FIG. 7, only radiation path 218c passes through deep lesion 210. Thus, only emerging radiation 216c may correspond to and be attenuated by water absorption in deep lesion 210.

According to some embodiments, a connection between measured absorption and differences in concentration of subcutaneous liquids may be described with reference to a modified Beer-Lambert law:

$$A(\lambda) = -\log[I(\lambda)/I_0(\lambda)] = \left(\varepsilon_{water}C_{water} + \sum_i \varepsilon_i \cdot C_i + \mu_S\right) \cdot \langle L \rangle$$

where $I_0(\lambda)$ is a measured source intensity, $I(\lambda)$ is a measured reflected intensity, $A(\lambda)$ is the measured absorption (attenuation), $\varepsilon_{water}$ is the absorptivity coefficient of water, $C_{water}$ is the concentration of water, and $\varepsilon_i$ and $C_i$ are the absorptivity coefficients and concentrations of different absorbing compounds. The path length $\langle L \rangle \sim$ (F·d) represents the total mean optical path in the tissue (e.g., in units of centimeters), where d is the distance between the point of incident radiation 214 and one of emerging radiation 216a, 216b, or 216c, and F is a scaling factor (related to the optical path length). The scattering coefficient may be expressed as $\lambda_s = \lambda_{s0}(1-g)$, where g is the scattering anisotropy.

For example, it may be assumed that the ratio for a penetration depth below tissue surface 22 may be twice the lateral distance d between the points of incident radiation 214 and the emerging radiation 216a, 216b, or 216c.

Differences in concentration of subcutaneous liquids may be estimated from the slope ($\Delta A/\Delta d$) of the attenuation with respect to distance d, where $A_1 - A_2 \equiv \Delta A = \varepsilon \cdot (\Delta C \cdot \langle L \rangle)$, with $A_1$ and $A_2$ representing differential absorptions $A_{Diff}$ as described above that are measured with two different lateral distances d between incident radiation 214 and emerging radiation 216a, 216b, or 216c.

In some embodiments, the change in differential measurements may be analyzed to obtain $\Delta A/\varepsilon = \Delta C \langle L \rangle$. When the relationship between path length $\langle L \rangle$ and lateral distance d is known, the measurements may be analyzed to yield a change in concentration of water.

According to some embodiments, Raman spectroscopy may be employed to analyze the measurement data. In Raman spectroscopy a complementary scattering mechanism to excite the molecules into the vibrational states may be achieved via the visible excitation wavelengths. Raman scattering may be an inelastic scattering which is usually generated by intensive monochromatic light (e.g., laser) in the visible, near infrared, or near ultraviolet (UV) region. The energy of laser photons may be changed after the excitation laser interacts with the vibrating molecules or the excited electrons in the sample. As a spontaneous effect, photons may transfer the excitation energy to change the molecule from the ground state to a virtual state. The excited molecule may then return to a different rotational or vibrational state after emitting a photon.

As may be apparent to one of ordinary skill in the art, the difference between wavelengths of photons in the incident wavelength $\lambda_0$ (excitation wavelength) and the scattered light is known as a Raman shift. It is related to characteristic oscillation frequencies of the molecule, and may correspond to the oscillations of a single molecular bond or the larger fragment of a molecular network. For $\lambda_0$ far from the molecule absorption band, intensity of the Raman signal may be inversely proportional to $\lambda_0^4$ so application of a VIS or UV laser as the excitation source may be more effective than an IR one if the intensity of Raman scattering was considered. However, practical efficiency of Raman scattering versus excitation wavelength may also depend on dimensions of the investigated structures.

Moreover, fluorescence induced by the laser beam may be also taken into account. Fluorescence is the strongest for the excitation wavelength $\lambda_0$ range extending from 270 to 700 nm but its influence can be different for various materials. It is particularly strong for organic materials, so the excitation range in VIS and near UV is not appropriate for their sampling.

In some embodiments, application of NIR lasers (e.g., in the range of 785-1064 nm) may be effective with selection of appropriate detector types (e.g., InGaAs, MCT, etc.) that can ensure high efficiency of the measurement system in a wide Raman range of 800 cm$^{-1}$ to 4000 cm$^{-1}$. Raman range of systems using such detectors may begin at about 800 cm$^{-1}$ for excitation wavelength equal to 830 nm.

In some embodiments, a measurement system (such as reflection measurement system 200 shown in FIG. 6A) to employ Raman spectroscopy may include at least one light source (e.g., such as source unit 202 shown in FIG. 6A). The source unit may include a diode laser (e.g., ~100 mW), light emitting diodes (LEDs) and/or a combination thereof. In some embodiments, Raman measurement system may include at least one light sensor (e.g., such as detection unit 204 shown in FIG. 6A). The light sensor may include a thermoelectric cooled charge coupled detector (CCD) and/or a spectrograph. In some embodiments, the Raman measurement system may include optical elements (e.g., such as optics 18a, 18b shown in FIG. 6A) with at least one of beam expanding/focusing lenses, laser-line filter, dichroic mirrors, holographic rejection (notch) filters, low-pas filter, and fibers. In some embodiments, in order to reduce the influence of background fluorescence signal, the 830 nm excitation wavelength may be used. According to some embodiments, Raman measurement system may indicate a change in concentration of a chemical compound within the tissue, for example due to deep tissue injury after calibration with healthy tissue is carried out.

According to some embodiments, a Raman measurement system may include at least one processor (such as controller 28 shown in FIG. 1A) and/or communicate with at least one processor (such as external processing device 30 shown in FIG. 1A) so as to allow analysis of the measured data according to Raman spectroscopy. In some embodiments, such analysis may include measurements of the distance between the light source and the light sensor. In some embodiments, such analysis may allow determination of liquid accumulation and/or determination of concentration of chemical compounds within the tissue (e.g., myoglobin, triglycerides, proteins, etc) and thereby determine deep tissue injuries if a change in the concentration corresponds to deep tissue injuries. In some embodiments, such analysis may allow determination of at least one substance secreted as a result of a deep tissue injury.

The Raman intensity may be $10^{-6}$ to $10^{-9}$ times less than that of Rayleigh scattering. Therefore, well-controlled high-power light sources (e.g., ~100 mW) and sufficient accumulation time (e.g., tens of a second) may be required in order to produce a sufficient number of Raman-scattering photons. In the IR spectroscopy, abundance of water in most biological environments, a very strong IR absorption by water may interrupt the emitted photons of the target. In contrast, a weak Raman scattering by water may have detection of bio-molecular signals in water-abundance environments, such as body fluids, cells and/or other tissues.

According to some embodiments, a controlled cyclic change in external conditions applied on a region of the skin may also allow determination of deep tissue injuries. In some embodiments, applying pressure (e.g., measuring with a pressure sensor) in varying magnitude and/or applying heat (e.g., measuring with a temperature sensor) in varying magnitude may cause different absorption and/or scattering of radiation in tissues with deep tissue injuries (compared to absorption and/or scattering in healthy tissue). For example, pressure may be applied in a periodical (e.g., sinusoidal) regime to determine presence of a deep tissue injury.

In some embodiments, an at least partially transparent (to visible and/or IR radiation) biodegradable element, for instance an elastomer or other soft plastic, may be placed upon the at least one radiation detector as a cover so as to allow protection of sensors (e.g., from gels applied on the skin). In some embodiments, such biodegradable element may be transparent at least 90%.

Unless explicitly stated, the method embodiments described herein are not constrained to a particular order in time or chronological sequence. Additionally, some of the described method elements can be skipped, or they can be repeated, during a sequence of operations of a method.

Various embodiments have been presented. Each of these embodiments may of course include features from other embodiments presented, and embodiments not specifically described may include various features described herein.

The invention claimed is:

1. A method for noninvasive analysis of tissue, the method comprising:
    irradiating, with at least one source of infrared radiation, a surface of the tissue with short wave infrared (SWIR) radiation in a first spectral band that is strongly absorbed by water, and with SWIR radiation in a second spectral band such that an interaction of the radiation in both spectral bands with a component of the tissue other than water is substantially identical;
    measuring, with at least one radiation detector, an intensity of the radiation that emerges from the tissue in each of the spectral bands;
    determining change in at least one of shape and intensity of signals received by the at least one radiation detector;
    calculating a relative absorption by the tissue of radiation in one of the first and second spectral bands relative to absorption by the tissue of radiation in the other of the first and second spectral bands; and
    determining, by a processor, a subcutaneous deep tissue injury under intact skin in which liquids accumulate subcutaneously, in accordance with the calculated relative absorption and in accordance with determined change in the received signal,
    wherein the interaction of the radiation comprises at least one of absorption and scattering.

2. The method of claim 1, wherein the first spectral band is in the wavelength range of 1400 nm to 1500 nm, and wherein the second spectral band is in the wavelength range of 1000 nm to 1350 nm or 1500 nm to 2100 nm.

3. The method of claim 1, further comprising applying pressure on surface of the tissue in a periodical regime.

4. The method of claim 1, wherein a gap in wavelength between the first and second spectral bands is less than 200 nm.

5. The method of claim 1, wherein measuring the intensity comprises measuring the intensity of the radiation that is transmitted across the tissue.

6. The method of claim 5, wherein the tissue comprises tissue of a finger or an ear.

7. The method of claim 1, wherein measuring the intensity comprises measuring the intensity of the radiation that is reflected by the tissue.

8. The method of claim 1, wherein determining the subcutaneous deep tissue injury comprises determining a concentration of a substance in blood within the tissue.

9. The method of claim 8, wherein the substance is an introduced substance.

10. A system for noninvasive analysis of tissue, the system comprising:
    at least one source of infrared radiation to irradiate the tissue, the infrared radiation including SWIR radiation in a first spectral band that is strongly absorbed by water, and including radiation in a second spectral band such that an interaction of the radiation in both spectral bands with a component of the tissue other than water is substantially identical;
    at least one radiation detector to measure an intensity of radiation in each of the two spectral bands that emerges from the tissue; and
    a processor that is configured to calculate a relative absorption by the tissue of radiation in one of spectral bands relative to absorption by the tissue of radiation in the other of the spectral bands and determine a subcutaneous deep tissue injury under intact skin in which liquids accumulate subcutaneously in accordance with the calculated relative absorption,
    wherein the interaction of the radiation comprises at least one of absorption and scattering.

11. The system of claim 10, wherein said at least one radiation detector is configured to measure the intensity of the radiation that emerges from a surface of the tissue that is irradiated by said at least one radiation source.

12. The system of claim 11, wherein said at least one radiation detector is configured to measure the intensity of the radiation that emerges from the surface of the tissue at a plurality of lateral distances from said at least one radiation source.

13. The system of claim 12, wherein said at least one radiation detector comprises a plurality of radiation detectors separated by different lateral distances from said at least one radiation source.

14. The system of claim 10, wherein said at least one radiation detector is configured to measure the radiation that emerges from a surface of the tissue that is substantially opposite a surface of the tissue that is irradiated by said at least one radiation source.

15. The system of claim 10, wherein said at least one radiation source comprises two radiation sources, one of the sources being configured to emit radiation in the first spectral band and the other being configured to emit radiation in the second spectral band.

16. The system of claim 10, wherein said at least one radiation detector comprises two radiation detectors, one of the detectors being configured to measure an intensity of radiation in the first spectral band and the other being configured to measure an intensity of radiation in the second spectral band.

17. The system of claim 10, comprising a dispersive element to separate spectral components of the infrared radiation and a micro-mirror array, the micro-mirror array configured to direct a selected spectral component of the infrared radiation to the tissue or to said at least one radiation detector.

18. The system of claim 10, wherein the first spectral band is in the wavelength range of 1400 nm to 1500 nm, and wherein the second spectral band is in the wavelength range of 1000 nm to 1350 nm or 1500 nm to 2100 nm.

19. A method for determining a deep tissue injury, the method comprising:
    irradiating, with at least one source of infrared radiation, a surface of the tissue with SWIR radiation in a first spectral band in the wavelength range 1300 nm to 1430 nm, and with SWIR radiation in a second spectral band such that an interaction of the radiation in both spectral bands with a component of the tissue other than water is substantially identical;
    measuring, with at least one radiation detector, an intensity of the radiation that emerges from the tissue in each of the spectral bands;
    calculating a relative absorption by the tissue of radiation in the two spectral bands; and
    determining a subcutaneous deep tissue injury under intact skin in which liquids accumulate subcutaneously in accordance with the calculated relative absorption,
    wherein the interaction of the radiation comprises at least one of absorption and scattering.

\* \* \* \* \*